(12) United States Patent
Gibson

(10) Patent No.: US 8,718,795 B2
(45) Date of Patent: May 6, 2014

(54) SECURING AN IMPLANTED MEDICAL DEVICE IN A PATIENT

(75) Inventor: Peter Gibson, South Coogee (AU)

(73) Assignee: Cochlear Limited, University, NSW (AU)

( * ) Notice: Subject to any disclaimer, the term of this patent is extended or adjusted under 35 U.S.C. 154(b) by 1364 days.

(21) Appl. No.: 12/422,038

(22) Filed: Apr. 10, 2009

(65) Prior Publication Data

US 2009/0254163 A1      Oct. 8, 2009

Related U.S. Application Data

(63) Continuation-in-part of application No. 12/052,193, filed on Mar. 20, 2008.

(60) Provisional application No. 60/918,917, filed on Mar. 20, 2007.

(30) Foreign Application Priority Data

Apr. 11, 2008   (AU) .............................. 2008901802

(51) Int. Cl.
    *A61N 1/05*    (2006.01)
(52) U.S. Cl.
    USPC ........................................................ 607/137
(58) Field of Classification Search
    USPC ............ 607/137, 126, 128; 600/25; 623/1.23
    See application file for complete search history.

(56) References Cited

U.S. PATENT DOCUMENTS

| | | |
|---|---|---|
| 4,487,210 A | 12/1984 | Knudsen et al. |
| 4,532,930 A | 8/1985 | Crosby et al. |
| 4,608,057 A | 8/1986 | Davis et al. |
| 4,645,504 A | 2/1987 | Byers |
| 4,795,426 A | 1/1989 | Jones |
| 4,892,108 A | 1/1990 | Miller et al. |
| 4,898,183 A | 2/1990 | Kuzma |
| 5,143,090 A | 9/1992 | Dutcher et al. |
| 5,267,968 A | 12/1993 | Russo |
| 6,070,105 A | 5/2000 | Kuzma |
| 6,119,044 A | 9/2000 | Kuzma |

(Continued)

FOREIGN PATENT DOCUMENTS

| | | |
|---|---|---|
| AU | 2006252212 | 7/2007 |
| EP | 1972359 | 9/2008 |

(Continued)

OTHER PUBLICATIONS

AT Office Action issued in T 576/2009 dated Nov. 4, 2010 (4 pages).

(Continued)

*Primary Examiner* — Christopher D Koharski
*Assistant Examiner* — Michael Carey
(74) *Attorney, Agent, or Firm* — K&L Gates, LLP

(57) ABSTRACT

An apparatus and method for implanting and securing an implanted medical device in a recipient. The implantable medical device of the generally includes a stimulating lead assembly that comprises an elongate carrier member having at least one stimulating element positioned thereon. The stimulating lead assembly further has an expandable portion thereon configured to be inserted into said reference structure in a first dimension, expand to a second dimension, and interact with a portion of the reference structure to help longitudinally secure the carrier member in the recipient.

32 Claims, 9 Drawing Sheets

(56) References Cited

U.S. PATENT DOCUMENTS

| | | | |
|---|---|---|---|
| 6,163,729 | A | 12/2000 | Kuzma |
| 6,259,951 | B1 | 7/2001 | Kuzma et al. |
| 6,308,101 | B1 | 10/2001 | Faltys et al. |
| 6,498,954 | B1 | 12/2002 | Kuzma et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,628,991 | B2 | 9/2003 | Kuzma et al. |
| 6,697,674 | B2 | 2/2004 | Leysieffer |
| 6,889,094 | B1 | 5/2005 | Kuzma et al. |
| 7,146,227 | B2 | 12/2006 | Dadd et al. |
| 7,194,314 | B1 | 3/2007 | Richter et al. |
| 2002/0123505 | A1* | 9/2002 | Mollison et al. .............. 514/291 |
| 2002/0156513 | A1 | 10/2002 | Borkan |
| 2003/0078516 | A1* | 4/2003 | Abbasi et al. ................. 600/559 |
| 2004/0225336 | A1 | 11/2004 | Milojevic et al. |
| 2004/0236390 | A1* | 11/2004 | Dadd et al. ...................... 607/55 |
| 2005/0139016 | A1 | 6/2005 | Yamanaka et al. |
| 2005/0256561 | A1 | 11/2005 | Gantz et al. |
| 2007/0135884 | A1 | 6/2007 | Risi |
| 2007/0162098 | A1* | 7/2007 | Risi et al. ...................... 607/137 |
| 2008/0154339 | A1* | 6/2008 | Carter ............................ 607/57 |
| 2008/0234793 | A1 | 9/2008 | Gibson |
| 2009/0254163 | A1 | 10/2009 | Gibson |

FOREIGN PATENT DOCUMENTS

| | | |
|---|---|---|
| WO | WO 96/31087 | 10/1996 |
| WO | WO 97/26943 | 7/1997 |
| WO | WO 00/69513 | 11/2000 |
| WO | WO 00/71063 | 11/2000 |
| WO | WO 02/078575 | 10/2002 |
| WO | WO 03/024153 | 3/2003 |
| WO | WO 2004004413 | 1/2004 |

OTHER PUBLICATIONS

AT Office Action issued in A 576/2009 dated Jun. 20, 2011 (4 pages).

Digisonic Convex Receiver document, believed to have been available as of late 2003 (1 page).

Extended European Search Report, Application No. 08005372.1, dated Dec. 12, 2008, (7 pages).

European Communication pursuant to Article 94(3) EPC, Application No. 08005372.1, dated May 16, 2011 (5 pages).

Balkany, et al., "Fixation of the Electrode Cable During Cochlear Implantation: The Split Bridge Technique", Laryngoscope 105: Feb. 1995, 217-218 (2 pages).

Cohen, "Surgical Techniques for Cochlear Implants", Cochlear Implants, edited by Waltzman et al., Thieme New York 2000, pp. 151-169, Chapter 8 (21 pages).

Cohen, et al., "Titanium Clip for Cochlear Implant Electrode Fixation", Clark & Cowan, International Cochlear Implant, Speech and Hearing Symposium, Melbourne 1994; Annals of Otology, Rhinology & Laryngology, Part 2, Supplement 166 Sep. 1995, 104(9);402-403.

Gantz et al., "Combining Acoustic and Electrical Hearing", Laryngoscope 113: Oct. 2003, pp. 1726-1730 (5 pages).

Gibson, et al. "Electrode Design Considerations for Reducing Trauma", 9th International Conference on Cochlear Implants and Related Sciences, Jun. 14-17, 2006, Vienna, Austria (16 pages).

Gibson, et al., Abstract for "Electrode Design Considerations for Reducing Trauma", 9th International Conference on Cochlear Implants and Related Sciences, Jun. 14-17, 2006, Vienna, Austria (1 page).

Lenarz, et al., "Hearing Conservation Surgery Using the Hybrid-L Electrode", Audiology and Neurotology Apr. 2009, 14(1);10, pp. 22-31 (10 pages).

Lenarz, Abstract for "Preservation of Residual Hearing with a New Straight Electrode", Jun. 14-17, 2006, Wiener Medizinische Wochenschrift, pp. 126-127 2006, (4 pages).

Lenarz, et al., "Temporal Bone Results and Hearing Conservation with a New Straight Electrode", First International Electro-Acoustic Workshop, Dec. 8-10, Toulouse 2005 (53 pages).

Lenarz, et al., "Temporal Bone Results and Hearing Preservation with a New Straight Electrode", presented at Cochlear Implantation, 1st International Electro-Acoustic Acoustic Workshop, Toulouse, Dec. 8-10, 2005, published at Audiol Neurotol 2006; 11(suppl 1) Oct. 6, 2006, pp. 34-41 (9 pages).

Xu, et al., "Temporal Bone Surgical Dissection for Cochlear Implantation", for Nucleus Freedom and Nucleus 24 Implants, sent to printers in late 2005, (65 pages).

* cited by examiner

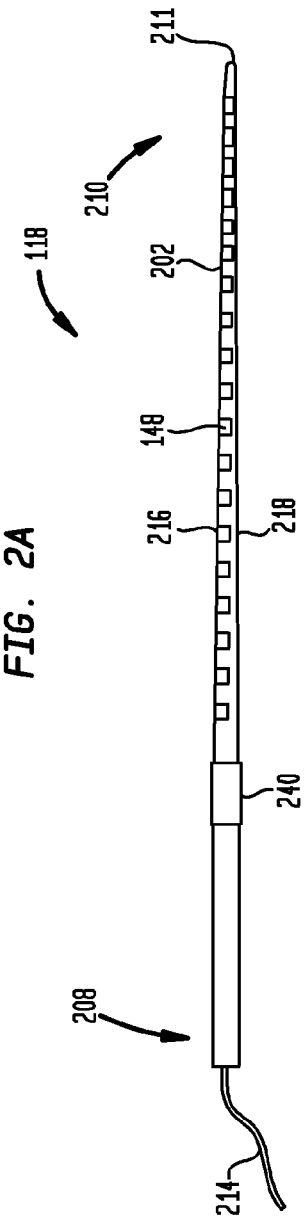
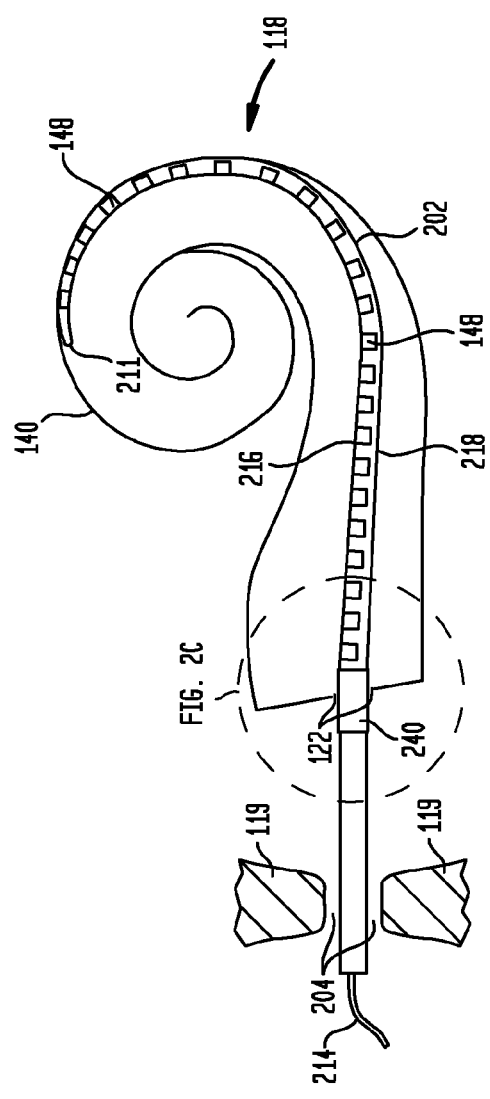
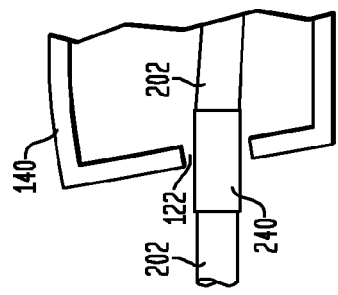

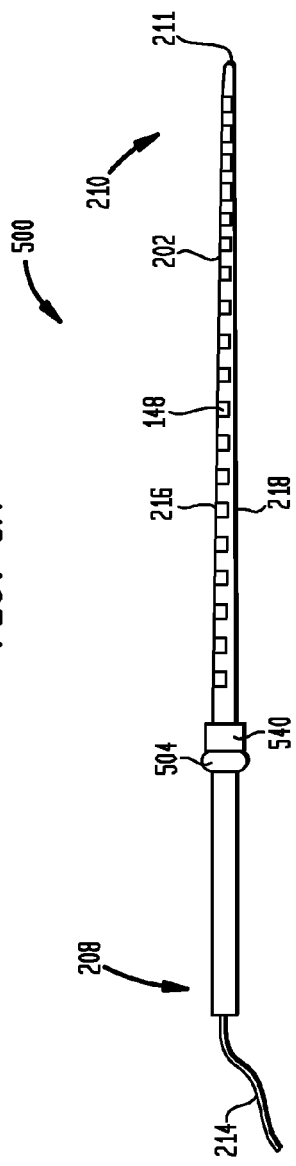
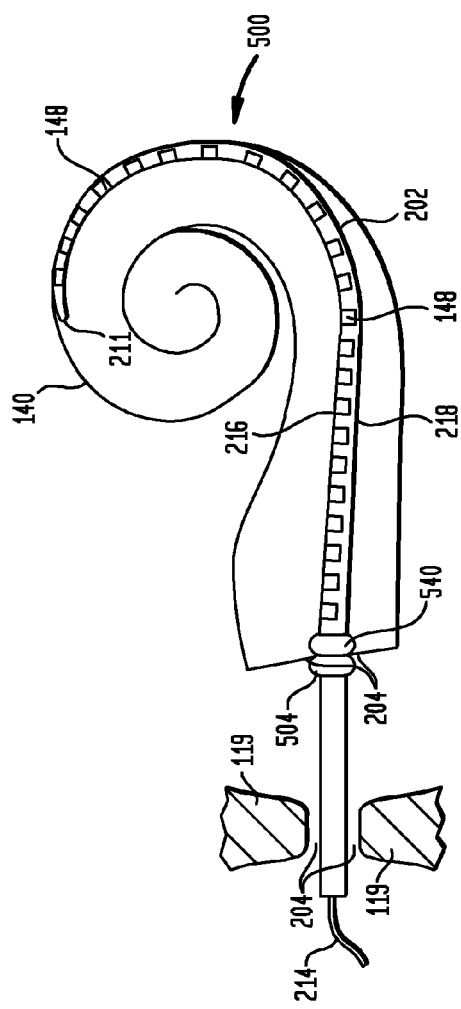
FIG. 5A
FIG. 5B

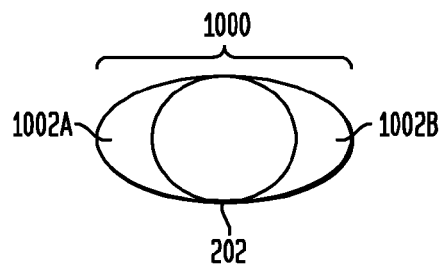
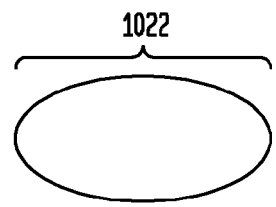
FIG. 10A   FIG. 10B
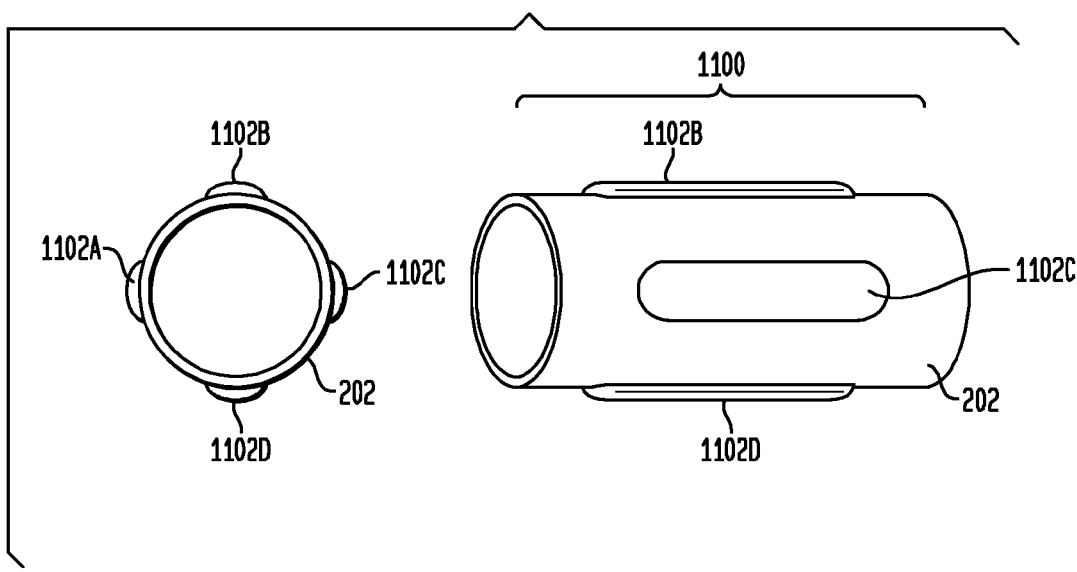
FIG. 11
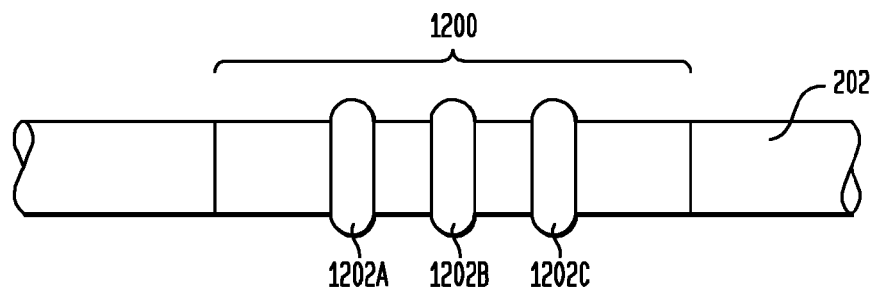
FIG. 12

SECURING AN IMPLANTED MEDICAL DEVICE IN A PATIENT

CROSS-REFERENCE TO RELATED APPLICATIONS

The present application claims the benefit of Australian Provisional Patent Application No. 2008901802, filed Apr. 11, 2008, which is hereby incorporated by reference herein. The present application is a continuation-in-part of U.S. patent application Ser. No. 12/052,193, filed Mar. 20, 2008, which claims the benefit of U.S. Provisional Application No. 60/918,917, filed Mar. 20, 2007, all of which are hereby incorporated by reference.

BACKGROUND

1. Field of the Invention

The present invention relates to an implantable device and, in particular, to securing an implantable tissue-stimulating device in a recipient.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from sensorineural hearing loss are thus unable to derive suitable benefit from conventional hearing aids. As a result, hearing prostheses that deliver electrical stimulation to nerve cells of the recipient's auditory system have been developed to provide persons having sensorineural hearing loss with the ability to perceive sound. Such stimulating hearing prostheses include, for example, auditory brain stimulators and cochlear prostheses (commonly referred to as cochlear prosthetic devices, cochlear implants, cochlear devices, and the like; simply "cochlear implants" herein.) As used herein, the recipient's auditory system includes all sensory system components that may be used to perceive a sound signal, such as hearing sensation receptors, neural pathways, including the auditory nerve and spiral ganglion, and regions of the brain used to sense sounds.

Most sensorineural hearing loss is due to the absence or destruction of the cochlea hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Such devices generally use an array of electrode contacts implanted into the scala tympani of the cochlea so that the electrodes may differentially activate auditory neurons that normally encode differential pitches of sound.

Auditory brain stimulators are used to treat a smaller number of recipients with bilateral degeneration of the auditory nerve. For such recipients, the auditory brain stimulator provides stimulation of the cochlear nucleus in the brainstem.

SUMMARY

In one aspect of the present invention, there is provided a stimulating lead assembly for implantation into a recipient through an opening in a reference structure in the recipient, comprising: an carrier member, having a proximal and a distal end and at least one stimulation element disposed along said carrier member; and an expandable portion being expandable from a first dimension to a second dimension, and configured to interact with the reference structure when said carrier member is implanted in the recipient and expanded to said second dimension.

In another aspect of the present invention, there is provided a method of implanting a stimulating medical device, comprising: preparing an appropriately configured opening in a reference structure of a recipient for implantation of an stimulating lead assembly comprising a carrier member and expandable portion; inserting said carrier member through said opening in the recipient; and expanding said expandable portion from a first dimension to a second dimension to interact with a portion of the reference structure to longitudinally secure said carrier member in the recipient.

BRIEF DESCRIPTION OF THE DRAWINGS

Illustrative embodiments of the present invention are described herein with reference to the accompanying drawings, in which:

FIG. 2A is a side view of a stimulating lead assembly comprising an expandable portion prior to insertion into cochlea, in accordance with embodiments of the present invention;

FIG. 2B is a side view of the stimulating lead assembly illustrated in FIG. 2A following insertion into a cochlea, but prior to expansion of the expandable portion, in accordance with embodiments of the present invention;

FIG. 2C is a magnified view of the expandable portion of FIG. 2B after insertion, but prior to expansion, in accordance with embodiments of the present invention;

FIG. 5A is a side view of a stimulating lead assembly, prior to insertion, comprising a stop member, in accordance with embodiments of the present invention;

FIG. 5B is a side view of a stimulating lead assembly, after insertion, comprising a stop member, in accordance with embodiments of the present invention;

FIG. 10A illustrates a cross-sectional view of an exemplary configuration for expandable portion that may expand from only a portion(s) of the circumference of a carrier member, in accordance with embodiments of the present invention;

FIG. 10B illustrates a cross-section of a slot shaped cochleostomy, in accordance with embodiments of the present invention;

FIG. 11 illustrates a cross-section and side view of an exemplary configuration for the expandable portion that comprises strips of expandable material, in accordance with embodiments of the present invention;

FIG. 12 illustrates a side view of an exemplary configuration for the expandable portion that comprises a plurality of rings, in accordance with embodiments of the present invention.

DETAILED DESCRIPTION

Aspects of the present invention are generally directed to securing an implantable medical device in a recipient (also referred to as a patient). The implantable medical device may be positioned adjacent to a reference structure in the recipient. An expandable portion of the stimulating medical device may be configured to expand during or after implantation to abut the reference structure to help secure the stimulating medical device relative to the reference structure.

Embodiments are described herein primarily in connection with one type of implantable medical device, a hearing prosthesis, and more specifically a cochlea implants. Cochlear implants generally refer to hearing prostheses that deliver electrical stimulation to the cochlear of a recipient. As used herein, cochlear implants may deliver electrical stimulation in combination with other types of stimulation, such as acoustic and/or mechanical stimulation. It would be appreciated that embodiments of the present invention may be implemented in any cochlear implant or other hearing prosthesis now know or later developed, including auditory brain stimulators (also known as auditory brainstem implants (ABIs)), or implantable hearing prostheses that acoustically or mechanically stimulate components of the recipient's middle or inner ear. Furthermore, it should be understood by those of ordinary skill in the art that embodiments may be implemented in implantable medical devices other than cochlear implants such as neurostimulators, cardiac pacemakers/defibrillators, etc. as well as other medical devices which temporarily or permanently implant, deliver or otherwise introduce into a recipient a therapeutic agent, sensor, electrode(s) or other active or passive component now or later developed.

Exemplary embodiments of a cochlear implant utilized in accordance with embodiments include a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, which are hereby incorporated by reference herein. Similarly, cochlear implants utilizing a short array of electrode contacts are described in commonly owned and co-pending U.S. patent applications Ser. Nos. 11/605,952 and 11/605,951, which are hereby incorporated by reference herein.

Figure 1:
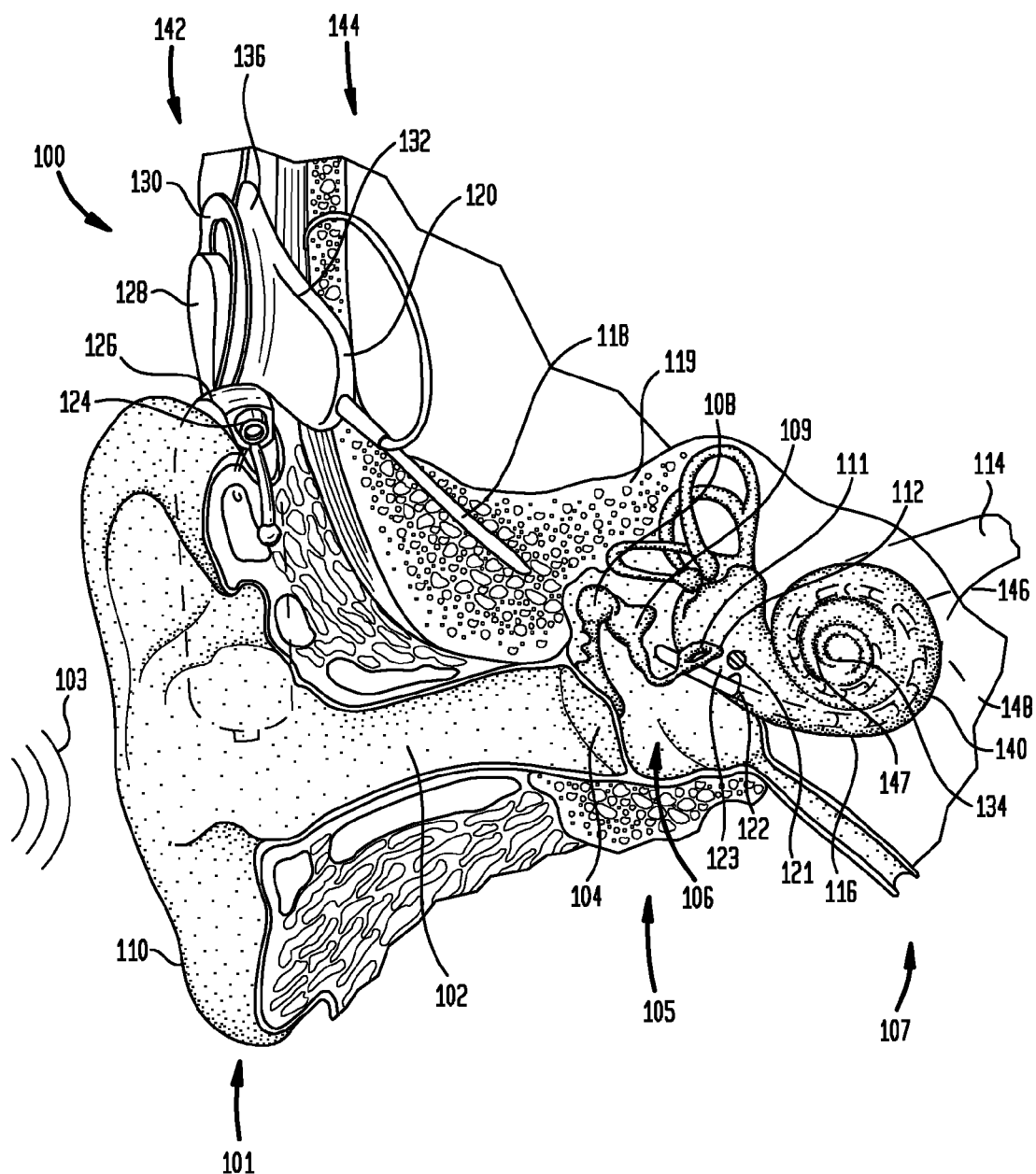
FIG. 1 is a perspective view of a cochlear implant in which embodiments of the present invention may be implemented.

FIG. 1 is perspective view of a cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound waves 103 is collected by auricle 110 and channeled into and through ear canal 102. Disposed across the distal end of ear cannel 102 is a tympanic membrane 104 which vibrates in response to sound waves 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound waves 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and a stimulating lead assembly 118. Internal receiver unit 132 comprises an internal coil 136, and preferably, a magnet (also not shown) fixed relative to internal coil 136. Internal receiver unit 132 and stimulator unit 120 are hermetically sealed within a biocompatible housing, sometimes collectively referred to as a stimulator/receiver unit. Internal coil 136 receives power and stimulation data from external coil 130, as noted above.

Stimulating lead assembly 118 has a proximal end connected to stimulator unit 120, and a distal end implanted in cochlea 140. Stimulating lead assembly 118 extends from stimulator unit 120 to cochlea 140 through temporal bone 119. In some embodiments stimulating lead assembly 118 may be implanted at least in basal region 116, and sometimes further into cochlea 140. For example, stimulating lead assembly 118 may extend towards apex 134 of cochlear 140. In certain circumstances, stimulating lead assembly 118 may be inserted into cochlea 140 via a cochleostomy 122. In other circumstances, a cochleostomy may be formed through round window 121, oval window 112, the promontory 123 or through an apical turn 147 of cochlea 140. As used herein the term "stimulating lead assembly," refers to any device capable of providing stimulation to a recipient, such as, for example, electrical or optical stimulation. A such, it should be understood that stimulating lead assembly 118 merely provides one embodiment of an exemplary stimulating lead assembly, and other types of stimulating lead assemblies may be used in other embodiments.

Stimulating lead assembly 118 comprises a longitudinally aligned and distally extending array 146 of electrode contacts 148, sometimes referred to as array of electrode contacts 146 herein, disposed along a length thereof. In most practical applications, array of electrode contacts 146 is integrated into stimulating lead assembly 118. As such, array of electrode contacts 146 is referred to herein as being disposed in stimulating lead assembly 118.

Stimulator unit 120 generates stimulation signals which are applied by electrode contacts 148 to cochlea 140, thereby stimulating auditory nerve 114. Stimulating lead assembly 118 preferably is positioned in cochlea 140 upon or immediately following implantation into cochlea 140. It is also desirable that stimulating lead assembly 118 be configured such that the insertion process causes minimal trauma to the sensitive structures of cochlea 140. Typically, stimulating lead assembly 118 is pre-curved, held in a substantially straight configuration at least during the initial stages of the implantation procedure, and then permitted to conform to the natural shape of the cochlea during and subsequent to implantation.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

The below discussed embodiments help minimize the risk of damage to the delicate structure of the cochlea on and following implantation of stimulating lead assembly 118 by helping secure stimulating lead assembly 118 upon insertion of stimulating lead assembly 118 into cochlea 140.

FIGS. 2A-C are side views of an embodiment of electrode assembly 118 comprising an expandable portion 240, prior to expansion. As will be discussed below, expandable portion 240 may help secure stimulating lead assembly 118 after implantation in the recipient. FIG. 2A illustrates stimulating lead assembly 118 prior to insertion into cochlea 140. FIG. 2B illustrates a view of stimulating lead assembly 118 following insertion, but prior to expansion of expandable portion 240. FIG. 2C illustrates a magnified view of the expandable portion 240 after insertion, but prior to expansion.

As illustrated, stimulating lead assembly 118 comprises a carrier member 202 that includes an expandable portion 240, a distal end 210, and a proximal end 208. Distal end 210 terminates in tip 211, and is adapted to be implanted furthest into cochlea 140. A plurality of spaced-apart stimulation elements 148, such as electrode contacts, are mounted or disposed on or in carrier member 202 between expandable portion 240 and tip 211. It should be appreciated that as used herein, particular combinations of the terms mounted/disposed, in/on, etc., are not to be interpreted to refer to any particular manufacturing technique or structural relationship. Extending from proximal end 208 of carrier member 202 is a lead 214. As used herein, the term stimulation element refers to any component, item, part, or device capable of providing stimulation, such as electrical or optical stimulation. Carrier member 202 may be manufactured from a silicone material, such as Silastic MDX 4-4210. Lead 214 physically and electrically connects stimulating lead assembly 118 with stimulator unit 120 (FIG. 1).

Stimulating lead assembly 118 may have a diameter of 0.8 mm (excluding expandable portion 240) in the region intended to be positioned adjacent to the boney wall of cochlear 240. Prior to expansion, expandable portion 240 may have a diameter slightly larger than that of stimulating lead assembly 118 immediately surrounding expandable portion 240 (e.g., a diameter of 0.9 mm). Or, for example, expandable portion 240 may also have a diameter equal to or less than that of the neighboring portions of stimulating lead assembly 118 (i.e., 0.8 mm). It should be noted that these diameters are exemplary only and in other embodiments, other sizes may be used. For example, in another embodiment, stimulating lead assembly 118 including expandable portion 240, prior to expansion, may have a constant diameter of 0.6 mm. Further, although stimulating lead assembly 118 is illustrated as having a cylindrical cross-sectional shape that tapes towards tip 211, it should be understood that stimulating lead assembly 118 may have other shapes, such as rectangular or square cross-sectional shape, a non-tapering shape, etc.

As shown in FIG. 2B, stimulating lead assembly 118 may be implanted into cochlea 140 through an opening 204 in temporal bone 119 and through an aperture in cochlea 140. The aperture may be, for example, oval window 112, round window 121 or a cochleostomy 122, as described above with reference to FIG. 1. In this description, reference will be made to cochleostomy 122 (FIG. 1); it should be appreciated, however, that other embodiments may be configured to be implanted in oval window 112, round window 121, or other natural or man-made aperture in cochlea 140.

As shown, expandable portion 240 may be only a small portion of stimulating lead assembly 118. For example, the longitudinal length of expandable portion 240 may be only slightly larger than the width of the boney wall through which cochleostomy 122 passes. In one such embodiment, expandable portion 240 may have a length approximately 2 mm wider than the width of the boney wall of cochlea 140, which typically has a width on the order of 1 mm. Then, expandable portion 240 may be positioned such that no more than 1 mm of expandable portion 240 (after expansion) extends into cochlea 140 and approximately 1 mm is located outside cochlea 140. In one embodiment, expandable portion 240 may be marked by, for example, a physical or colored marker to aid the surgeon in placing expandable portion 240 inside cochleostomy 122.

Restricting expandable portion 240 to the area close to cochleostomy 122 may help prevent the risk of expandable portion 240 expanding too far into cochlea 140 and potentially causing trauma to the delicate cochlear structures such as the osseous and spiral laminar. As will be discussed in further detail below, expandable portion 240 may have different shapes and lengths in different embodiments, and in certain embodiments may have a length greater or less than the width of the cochlea wall.

When implanted, the surface of carrier member 202 that faces the interior of cochlea 140 is referred to herein as the medial surface 216 of carrier member 202. The opposing side of carrier member 202, referred to herein as lateral surface 218, faces the external wall and bony capsule (not shown) of cochlea 140. It should be understood that the terms medial surface, medial direction, and the like, are generally used herein to refer to the surfaces, features and directions toward the center of cochlea 140, while the terms lateral surface, lateral direction, and the like, are generally used herein to refer to surfaces, features and directions toward the exterior of cochlea 140.

As would be appreciated by those of ordinary skill in the art, electrode contacts 148 may be disposed in a linear or non-linear array on or in carrier member 202, and are typically positioned on or in carrier member 202 so as to align with predetermined regions of tonotopically mapped cochlea 140 when implanted in cochlea 140. In alternative embodiments, electrode contacts 148 are implemented as described in U.S. patent application Ser. Nos. 11/605,951 (filed Nov. 30, 2006), 12/065,209 (filed Oct. 14, 2008), or 11/650,960 (filed Nov. 30, 2006), each of which are hereby incorporated by reference herein.

In an embodiment, electrode contacts 148 are half-band electrodes disposed in or on medial surface 216 of carrier member 202. It should be appreciated, however, that any electrodes now or later developed suitable for a particular application may be used in alternative embodiments. For example, in one alternative embodiment, electrode contacts 148 are banded electrodes extending substantially around the circumference of carrier member 202. In another embodiment, electrodes 212 do not laterally extend to or around the edges of carrier member 202. Typically, each electrode contact 148 is arranged such that its exposed surface is substantially parallel to a longitudinal axis 224 of carrier member 202. It should be appreciated, however, that other locations and orientations may be implemented in alterative embodiments. It should further be appreciated that the quantity of electrode contacts 148 may vary from as few as one or two to as many as twenty-four or more.

In certain embodiments, at least one electrode contact 148 has a surface that is at least adjacent medial surface 216 of carrier member 202. In other embodiments, however, the surfaces of electrode contacts 148 may be raised above or recessed into medial surface 216 of carrier member 202. It should be appreciated, however, that any embodiment of electrode contacts 148 may be implemented. Electrode contacts 148 may be manufactured from a biocompatible conductive material such as platinum, although other materials or combinations of materials may be used. In certain alternative embodiments electrode contacts 148 are coated with a biocompatible covering that does not interfere with the transfer of stimulation signals to cochlea 140.

A variety of surgical methods may be used to implant a stimulating lead assembly 118 in a recipient, including a mastoidectomy and facial recess approach, a transcanal approach, or a combination thereof, depending upon the particular recipient anatomy, recipient needs and surgeon's discretion. For ease of description, embodiments of the present invention will be described with reference to implantation using a facial recess approach.

Figure 3A:
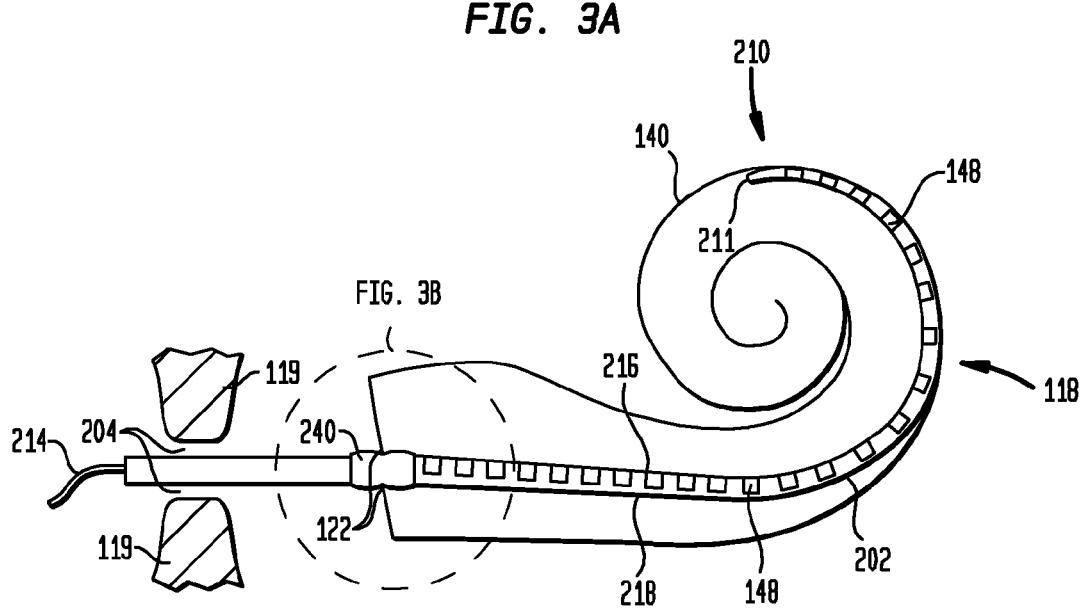
FIG. 3A is a side view of the stimulating lead assembly of FIG. 2A, after implantation and expansion of the expandable portion, in accordance with embodiments of the present invention.
Figure 3B:
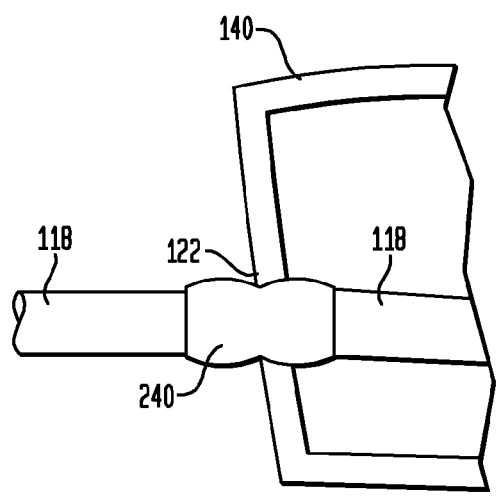
FIG. 3B is a magnified view of the expandable portion of FIG. 3A after implantation and expansion, in accordance with embodiments of the present invention.

FIGS. 3A-3B illustrate stimulating lead assembly 118 after expansion of expandable portion 240, in accordance with an embodiment. FIG. 3A illustrates a view of stimulating lead assembly 118 extending through mastoid bone 119 and cochleostomy 122; and, FIG. 3B illustrates a magnified view of expandable portion 240 after expansion. As illustrated, expandable portion 240 may expand so that it contacts the bone of cochlea 140 surrounding cochleostomy 122. This may serve to effectively seal and stabilize (i.e., secure) stimulating lead assembly 118 in cochlea 140.

Inserting unexpanded expandable portion 240 into cochleostomy 122 so that it is adjacent to the boney wall of cochlea 140 and allowing it to expand to abut the boney wall of cochlea 140 may help secure stimulating lead assembly 118 in cochlea 140. Securing stimulating lead assembly 118 helps reduce the risk that stimulating lead assembly 118 may withdraw from or otherwise migrate in or from cochlea 140, which could potentially result in damage to the sensitive cochlea structures and/or reduced effectiveness of the applied stimulation. Further, the electrode lead or other electrical conductors used in cochlear implants are typically robust to help cope with the body environment, these electrode leads have the potential to impart a slight force on the cochlear implant when implanted that could result in undesirable movement of the cochlear implant relative to the cochlea. Use of an expandable portion, such as the above discussed expandable portion 240, may help counteract this force and maintain the cochlear implant in its desired position relative to the cochlea.

Sealing stimulating lead assembly 118 in cochlea 140 may help prevent cochlear fluid, such as perilymph, from leaking out of cochlea. Additionally, because expandable portion 240 may expand over a short duration of time, expandable portion 240 may more quickly seal cochlea 140 than prior techniques for sealing a cochea, such as using fibrous tissue, which may take a significant amount to integrate with the surrounding tissue.

In an embodiment, in which expandable portion 240 has a diameter of 0.8 mm prior to expansion, expandable portion 240 may have a diameter of approximately 1 to 1.2 mm after expansion. Or, for example, in an embodiment in which the expandable portion has a diameter of 0.6 mm prior to expansion, expandable portion 240 may have a diameter of approximately 0.8 to 1.0 mm after expansion. It should be noted that these diameters are exemplary only and that other diameters may be used.

In certain embodiments, expandable portion 240 comprises, for example, a portion of carrier member 202 with a layer of expandable material applied to the exterior surface of carrier member 202. The properties of this material may be such that the material expands (e.g., swells) upon exposure to bodily fluid and/or saline solution. The layer of expandable material deposited on the surface of carrier member 202 may be thin relative to the dimensions of stimulating lead assembly 118. The layer may be applied, for example with an applicator or sprayed onto carrier member 202. Or, for example, an appropriate portion of carrier member 202 may be dipped in the expandable material. In an alternative embodiment, carrier member 202 may have a recess formed therein to receive the layer of expandable material. While depicted in FIG. 2 with a diameter slightly greater than carrier member 202, the recess, if utilized, may have a depth such that the diameter of expandable portion 240 is no greater or even less than the diameter of stimulating lead assembly 118 adjacent expandable portion 240.

However, in other embodiments, rather than expandable portion 240 being a portion of carrier member 202 with a layer of expandable material, expandable portion 240 may be a separate member that is connected (either removably or non-removably) to carrier member 202. That is, stimulating lead assembly 118 may be formed using three pieces (a proximal carrier member piece, an expandable member, and a distal carrier member piece) with a proximal carrier member piece located proximal to the expandable member (i.e., expandable portion 240), a distal carrier member piece located distal to the expandable member, and the expandable member connecting the proximal and distal carrier member pieces. In such an example, the expandable member may comprise a lumen passing through the member through which the electrode leads (not shown) or other electrode conductors may pass. Further, in certain such embodiments, expandable portion 240 may have a cross-sectional shape that is similar to or matches the cross-sectional shapes of the distal and proximal carrier member pieces.

Or, in yet another embodiment, expandable portion 240 may be a collar that may be moved longitudinally along stimulating lead assembly 118. This collar may be positioned on carrier member 202 during manufacture, or, for example, by a surgeon during implantation of stimulating lead assembly 118. For example, expandable portion may be a separate collar or ring that may be slid over carrier member 202 by a surgeon prior to surgery. Then during surgery, the surgeon may position the collar or ring in cochleostomy 122.

As noted above, expandable portion 240 may comprise a material that expands on exposure to moisture, such as bodily fluids, sterile saline or other solutions. The material may be a biocompatible hygroscopic material such as soft hygroscopic polymeric or hydrogel material. As an example, the biocompatible material can be a natural polymer such as a glycosaminoglycan, for example, hyaluronic acid, chondroitin sulfate, and cellulose or a synthetic polymer, such as a hydrogel, poly(vinyl alcohol), poly(2-hydroxyethylmethylacrylate), and polyethylene oxide. Other possible materials include collagen, chitosan, alginate, a poly(acrylonitrile)-based hydrogel, poly(ethylene glycol)/poly(acrylic acid) (PEG/PAA) interpenetrating polymer network (IPN) hydrogel, polyethylene oxide-polybutylene terephthalate (PEO-PBT), a hyaluronic acid based hydrogel, high-molecular-weight polyacrylic acid (PAA) as a filler in a Silastic™ matrix, PVA/chitosan blends, poly(hydroxy ethylmethacrylate), poly(ethylene glycol) (PEG) hydrogels, tetraethylene glycol diacrylate, polyethylene glycol methacrylate (PEGMA), cross-linkable (2-hydroxyethyl methacrylate) (HEMA), and poly(methyl acrylate-co-hydroxyethyl acrylate) hydrogel. Use of a soft polymeric material, which may stretch and thin, may be beneficial should stimulating lead assembly 118 need to be extracted out of cochleostomy 122.

Or, for example, expandable portion 240 may comprise a shape memory material, such as Nitinol™, that swells or changes shape on exposure to body temperature. Or, in yet another embodiment, expandable portion 240 may comprise a material that expands on exposure to applied heat, a suitable source of electromagnetic radiation (e.g., UV light), an electric field, or other catalyst.

The degree to which expandable portion 240 expands may be chosen so that the when expanded, expandable portion 240 does not create excessive force or pressure on the surrounding boney wall of cochlea 140, which may result in bone resorption/necrosis or result in disruption to intracochlear structures located just inside cochleostomy 122. Further, the material selected for expandable portion 240 may be selected to have particular properties to control, for example, the onset and rate of expansion. For example, the material may be selected to have a particular rate of uptake of moisture and speed of expansion on exposure to a particular fluid, such as, body fluids and/or saline solution. The defined rate of moisture uptake may serve to define the rate of expansion of expandable portion 240. In yet another embodiment, a beneficial compound may be impregnated within or otherwise releasable from the expandable portion 240 on expansion. For example, an antibacterial drug can be impregnated in the material comprising the expandable portion 240 that may be released (e.g., by dissolving in the presence of a fluid) upon expansion of expandable portion 240. By helping secure the stimulating lead assembly 118 using a material that expands to its expanded dimensions in a relatively short amount of time, the surgeon may be able to complete the surgical implantation process in a shorter period of time, which may minimize the amount of time the cochlea is open during surgery and thus decrease the risk of damage to the cochlea's sensitive structures. This may be further beneficial in recipients that still have some residual hearing (e.g., particular frequencies).

In embodiments in which expandable portion 240 comprises a material that expands on exposure to fluids, the surgeon may keep the material dry prior to insertion, then after insertion and positioning of expandable portion 240 inside cochleostomy 122, the surgeon may permit expandable portion 240 to come into contact with body fluids and/or apply a solution (e.g., saline solution) to cause expandable portion 240 to begin expanding.

In another embodiment, expandable portion 240 may comprise multiple materials. For example, in an embodiment, expandable portion 240 may comprise an outer layer and an inner layer. The inner layer may comprise an expandable material, such as noted above, and the outer layer may comprise a material that serves to prevent or delay exposure of the inner layer to moisture. In one such embodiment, the outer layer may be a polymeric material that may dissolve on exposure to fluid or solution at a rate that provides sufficient time for the surgeon to position stimulating lead assembly 118 within the recipient. Such an outer layer may serve to prevent exposure of the expandable inner layer to fluid or solution following stimulating lead assembly 118 placement for a period of, for example, between 30 seconds and 5 minutes, preferably between 1 and 2 minutes. Then, on being exposed to the fluid or solution, the expandable inner layer may expand to its second dimension in a time of, for example, between 10 and 40 seconds, more preferably about 20 seconds.

In another embodiment, the outer layer may comprise a relatively moisture impervious membrane, such as a biocompatible elastomeric material (e.g., a suitable polyurethane) that seals the expandable inner layer and prevents moisture ingress until the membrane is breached. In such an embodiment, the surgeon or another person may breach the membrane with a suitable tool or, for example, the membrane could be provided with frangible seals that can be cut or ripped once the carrier membrane is in the desired position. In another such embodiment, the membrane may have one or more ports through which an appropriate solution, such as sterile saline solution, can be injected when desired. The injection of such a solution may cause expandable portion 240 to expand thus breaching the membrane. Use of such a relatively moisture impervious membrane may provide the surgeon with the ability to control the timing of the onset of expansion thus enabling the surgeon to properly position stimulating lead assembly 118 prior to initiating the expansion of expandable portion 240.

Referring again to FIG. 1, in an implantation procedure utilizing the facial recess approach, stimulating lead assembly 118 is inserted during an operation that usually takes between 2-3 hours, depending on the device to be implanted. An incision is made behind outer ear 101 to expose temporal bone 119. Temporal bone 119 consists of several segments (not shown) known as the squamous, the mastoid, the tympanic, the zygomatic and the petrous segment. Typically, traditional cochlear implants require the opening of the mastoid segment of temporal bone 119 which leads to middle ear 105.

Following the opening of the incision behind outer ear 101, a shallow recess is created in the mastoid to hold internal receiver unit 132 and stimulator unit 120. Next, additional amounts of the mastoid are removed. By removing this additional portion of the mastoid, the surgeon opens an area known as the facial recess. The facial recess is a concave portion of the inner side of the mastoid bone that opens to middle ear 105, and inner ear 107. As the facial recess is opened, the surgeon is able to access middle ear 105 and inner ear 107.

The surgeon then prepares cochleostomy 122 in cochlea 140 to allow implantation of stimulating lead assembly 118 into cochlea 140. As noted above, the opening may be formed through round window 112, oval window 121, the promontory or through the apical turn of cochlea 140. Stimulating lead assembly 118 is then gently threaded into the shell-like structure of cochlea 140. Depending in the type of implant used, the opening may either remain open to heal with scar tissue, or may be closed by the surgeon. The procedure is completed by closing the incision behind outer ear 101.

Cochleostomy 122 may be drilled so that it provides an opening into cochlea 140 that is slightly larger than the diameter of stimulating lead assembly 118. Thus, only a slight amount of expansion by expandable portion 240 may effectively seal and secure stimulating lead assembly 118 in cochlea 140 without producing an excessively high and undesirable amount of pressure on the bone surrounding cochleostomy 122.

Figure 4:
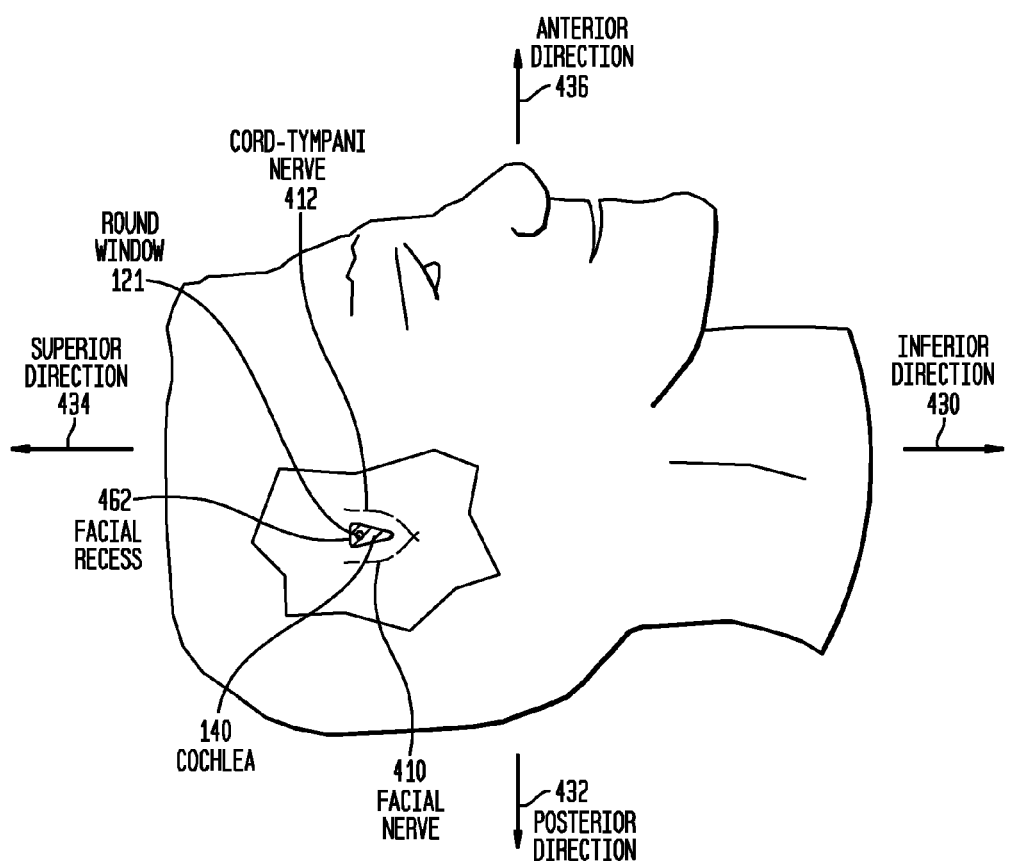
FIG. 4 is a perspective view of a recipient illustrating the location of implantation of a stimulating lead assembly in accordance with embodiments of the present invention.

FIG. 4 illustrates a perspective view of the right side of a recipient showing the location of implantation of certain embodiments of the stimulating lead assembly in accordance with the facial recess approach. It should be appreciated, however, that embodiments of the present invention are equally applicable to other implantation methods. Directional arrows 430, 432, 434 and 436 illustrate general directions in relation to the recipient. Directional arrow 430 illustrates the inferior direction, and refers to a direction that is towards the feet of the recipient. Directional arrow 432 illustrates the posterior direction, and refers to a direction that is towards the back of the recipient's head. Directional arrow 434 illustrates the superior direction, and refers to a direction that is towards the top of the recipient's head. Directional arrow 436 illustrates the anterior direction, and refers to a direction that is towards the front of the recipient's head.

As illustrated in FIG. 4, facial recess 462 is positioned between the facial nerve 410 and the cord-tympani nerve 412. Facial recess 462 may be opening 204 (FIG. 2). Facial nerve 410 is positioned posterior to facial recess 462, and cord-tympani nerve 412 is positioned anterior to facial recess 462. Visible behind facial recess 462 is round window 121 of cochlea 140. In some embodiments of the present invention, stimulating lead assembly 118 is configured to be implanted through facial recess 462 and into round window 121.

FIGS. 5A and 5B are side views of an embodiment of stimulating lead assembly comprising a stop member, in accordance with an embodiment. In FIGS. 5A-B stimulating lead assembly 118 is referred to as stimulating lead assembly 500. In FIG. 5A, the stimulating lead assembly is illustrated prior to insertion in a recipient's cochlea; FIG. 5B, following insertion. Stimulating lead assembly 500 comprises a carrier member 202 having a proximal end 208 and a distal end 210. Distal end 210 terminates in tip 211, and is adapted to be implanted furthest into cochlea 140. A plurality of spaced-apart electrode contacts 148 are disposed in carrier member 202 along medial surface 216 of carrier member 202 between expandable portion 540 and tip 211. The opposing side of carrier member 202 is referred to herein as lateral surface 218. Lead 214 extends from proximal end 208.

Attached to or integral with carrier member 202 are a stop member 504 and an expandable portion 540. Expandable portion 540 is positioned between stop member 504 and all, and, in embodiments in which not all electrodes 212 are to be inserted into cochlea 115, some of electrode contacts 148. Stop member 504 is positioned on carrier member 202 between proximal end 208 and expandable portion 540, and as illustrated, stop member 404 may be adjacent to expandable portion 540. Expandable portion 540 may comprise an expandable material, such as discussed above. Stop member 504 may be manufactured from a non-expandable material, such as silicone, and in embodiments may be a contiguous portion of carrier member 202. Further, stop member 504 may have a diameter greater than that of the adjacent portion of carrier member 202 and expandable portion 540, prior to expansion. Or, in other embodiments, stop member 540 may be manufactured from an expandable material, such as discussed above, that may be expanded during or after implantation of stimulating lead assembly 118 similar to the above-discussed expandable portion 240.

Stimulating lead assembly 500 may be surgically inserted using a similar mechanism as discussed above with reference to FIGS. 2-4. In this example, however, stop member 550 may be located along carrier member 202 in a position such that stimulating lead assembly 500 is properly positioned in cochlea 140 when stop member 540 abuts the boney wall of cochlea 140 surrounding cochleostomy 122. Thus, during implantation of stimulating lead assembly 500, the surgeon may insert carrier member 202 into cochlea 140 until stop member 504 contacts the exterior surface of cochlea 140 surrounding cochleostomy 122, thus indicating that stimulating lead assembly 118 is properly positioned. The surgeon may then allow expandable portion 540 to expand in order to seal and/or secure stimulating lead assembly 500. Stop member 504 may be, for example, a stop member such as described in U.S. patent application Ser. No. 12/052,193 filed Mar. 20, 2008, which is hereby incorporated by reference.

Figure 6:
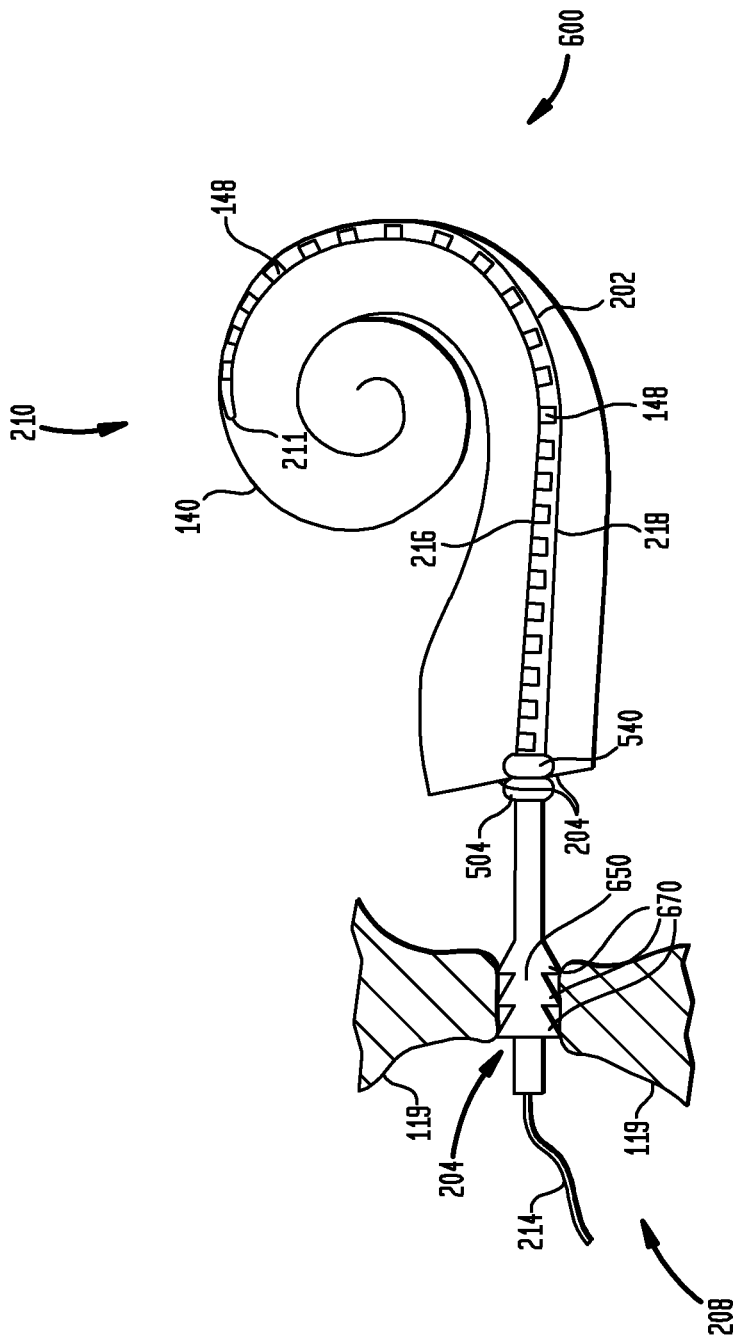
FIG. 6 is a side view of a stimulating lead assembly comprising a fixation structure, in accordance with embodiments of the present invention.

FIG. 6 is a side view of one embodiment of stimulating lead assembly 118, referred to herein as stimulating lead assembly 600, comprising a fixation structure, in accordance with an embodiment. Fixation structure 650 may help reduce the ability of stimulating lead assembly 600 to exit or rotate within cochlea 140 following implantation. In FIG. 6, stimulating lead assembly 600 is shown in an implanted position, and is viewed from an anterior direction of the recipient. Stimulating lead assembly 600 comprises a carrier member 202, having proximal end 208 and distal end 210, terminating in tip 211. A plurality of spaced-apart electrode contacts 148 are disposed in carrier member 202 along medial surface 216 of carrier member 202. The opposing side of carrier member 202 is referred to herein as lateral surface 218. Lead 214 extends from proximal end 208.

Attached to or integral with carrier member 202 are expandable portion 540 and stop member 504 as described above with reference to FIGS. 5A and 5B. Fixation structure 650 is positioned at or near proximal end 208 of carrier member 202 to substantially interact with at least a portion of the bone surrounding facial recess 204. In the specific embodiment shown in FIG. 6, fixation structure 650 comprises a series of circumferentially-extending projections 670. If circumferentially-extending projections 670 are viewed along a plane that extends longitudinally through fixation structure 650, each projection may have, for example, a substantially triangular cross-sectional shape.

Fixation structure 650 may comprise a material that expands in the presence of fluids (e.g., body fluids and/or saline solution), such as the above-discussed expandable materials (e.g., hygroscopic materials, multiple layers, etc.). In such an embodiment, a surgeon may insert stimulating lead assembly 118 into cochlea 140 with fixation structure 650 and expandable portion 540 in their unexpanded states. The surgeon may insert stimulating lead assembly 118 until stop 504 contacts the bone surrounding cochleostomy 122, such as was discussed above with reference to FIG. 5. Then, the surgeon may allow fixation structure 650, stop member 504, and/or expandable portion 540 to expand. Any of the above, techniques discussed with reference to FIG. 2 may be used in permitting fixation structure 650 and expandable portion 540 to expand, such as, for example, using an expandable portion comprising inner and outer layers, etc.

In FIG. 6, circumferentially-extending projections 670 are dimensioned to extend from carrier member 202 to bone 119 surrounding facial recess 204. The above-noted tendency of stimulating lead assembly 600 to exit cochlea 140 places pressure on fixation structure 650 to exit the recipient. However, the pressure from carrier member 202 causes circumferentially-extending projections 670 to further interact with bone 119. This interaction produces a longitudinal anchor force that substantially prevents longitudinal movement (that is, movement in a direction approximately parallel to the longitudinal axis of the device) of fixation structure 650 out of the recipient. This resulting longitudinal anchor force is a force along the longitudinal axis of stimulating lead assembly 600 in the direction of cochlea 140. The longitudinal anchor force maintains fixation structure 650 in bone 119 thereby retaining carrier member 202 in a desired position in cochlea 140. In other words, the longitudinal anchor force prevents substantial longitudinal movement of carrier member 202 out of cochlea 140.

As noted, embodiments of stimulating lead assembly 600 may include half-band electrodes. For optimal stimulation, a stimulating lead assembly utilizing half-band electrodes is preferably maintained in a desired position and orientation within cochlea 140. However, due to certain aspects of the implantation procedure, a rotational force may be created on stimulating lead assembly 600 that causes stimulating lead assembly 600 to twist within cochlea 140. If stimulating lead assembly 600 twists within cochlea 140, the half band electrodes will no longer be in a desired orientation for optimal stimulation. In such embodiments, fixation structure 650 may be configured to produce an additional anchor force that prevents rotation of stimulating lead assembly 600 within cochlea 140. This additional anchor force is referred to herein as a rotational anchor force. As stimulating lead assembly 600 attempts to twist within cochlea 140, the torque causes circumferentially-extending projections 670 to further interact with bone 119. This additional interaction produces a rotational anchor force that substantially prevents rotational movement of fixation structure 650. As a result of this rotational anchor force rotational movement substantial of carrier member 202 is also prevented.

In other embodiments, fixation structure 605 may be manufactured from a material that does not expand in the presence of fluids. For example, in one such embodiment, fixation structure 650 comprises a flexible material having a diameter that is larger than facial recess 204. In such embodiments, during implantation, flexible fixation structure 650 is forced in to facial recess 204 and is compressed therein. As fixation structure 650 attempts to exit cochlea 140, the compression of fixation structure 650 by bone 119 creates the longitudinal anchor force that prevents movement of fixation structure 650 out of cochlea 140. In such embodiments, fixation structure 650 may comprise a flexible component such as silicone, polyurethane, PTFE, etc.

In other embodiments, the longitudinal anchor force created by the interaction of fixation structure 650 and bone 119 may be the result of friction. As stimulating lead assembly 600 attempts to exit cochlea 140, the friction between fixation structure 650 and bone 119 produces the longitudinal anchor force that prevents movement of stimulating lead assembly 600. In certain embodiments, fixation structure 650 may have a rough or uneven surface that increases friction with bone 119.

As would be understood to those of ordinary skill in the art, the bone surrounding facial recess 204 is typically not a smooth surface, and likely has burrs and marks resulting from its interaction with surgical tools, as well due to the structural features of bone 119. For example, bone 119 naturally includes aerated sections that form openings in the bone. Such attributes of bone 119 tend to increase the friction between fixation structure 650 and bone 119. In further embodiments, the surface of bone 119 may be purposefully scored to further increase the friction with fixation structure 650.

In yet an alternative embodiment, fixation structure 650 may comprise a malleable material such as a metal or a hard plastic or a shape-memory material that changes shape upon heating to body temperature or other catalyst such has IR or UV light, to anchor itself into the recess in bone 119. In such embodiments fixation structure 650 may comprise materials such as titanium, platinum, stainless steel, chromium, nitinol, etc. In one particular embodiment, the shape-memory material comprises a shape-memory polymer. A further description of exemplary fixation structures is provided in the above-incorporated U.S. patent application Ser. No. 12/052,193 filed Mar. 20, 2008.

Figure 7:
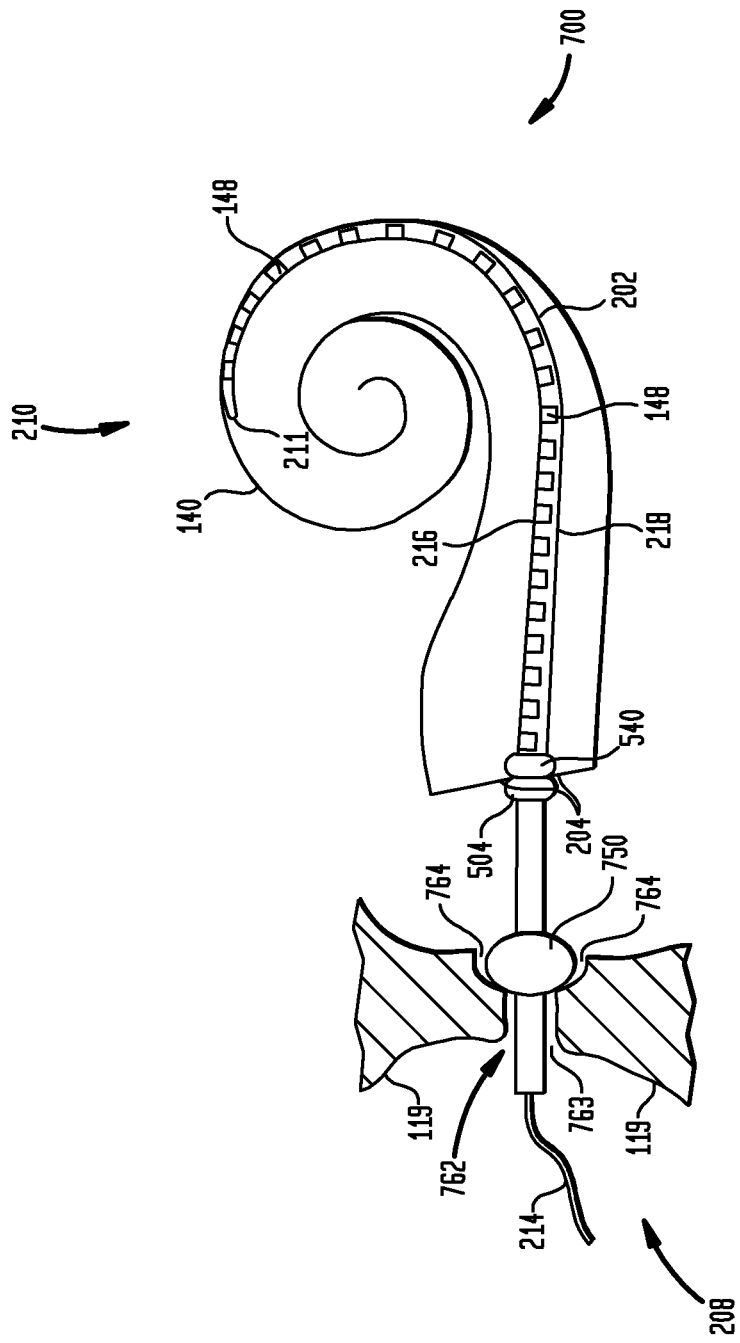
FIG. 7 is a side view of a stimulating lead assembly comprising an alternative fixation structure, in accordance with embodiments of the present invention.

FIG. 7 is a side view of an embodiment of stimulating lead assembly 118, referred to herein as stimulating lead assembly 700, configured to reduce the ability of stimulating lead assembly 700 to exit cochlea 140 following implantation. In FIG. 7, stimulating lead assembly 700 is shown in an implanted position, and is viewed from an anterior direction of the recipient. Stimulating lead assembly 700 comprises a carrier member 202, having proximal end 208 and distal end 210 terminating in tip 211. A plurality of spaced-apart electrode contacts 148 are disposed in carrier member 202 along medial surface 216 of carrier member 202. The opposing side of carrier member 202 is referred to herein as lateral surface 218. Lead 214 extends from proximal end 208. As in the embodiment of FIG. 7, embodiments of stimulating lead assembly 700 may include half-band electrodes.

Attached to or integral with carrier member 202 are expandable portion 540 and stop member 504 as described above with reference to FIGS. 5A and 5B, and fixation structure 750. Fixation structure 750 is positioned at or near proximal end 208 of carrier member 202 to substantially interact with at least a portion of the bone surrounding facial recess 762.

In the specific embodiment illustrated in FIG. 7, facial recess 762 may be shaped by the surgeon such that facial recess 762 has an outer portion 763 that is narrower than an inner portion 764 of facial recess 762. Fixation structure 750 may comprise a material that expands in the presence of fluids (e.g., body fluids and/or saline solution), such as the above-discussed expandable materials. In such an embodiment, a surgeon may insert stimulating lead assembly 118 into cochlea 140 with fixation structure 750 and expandable portion 540 in their unexpanded states. The surgeon may insert stimulating lead assembly 118 until stop 504 contacts the bone surrounding cochleostomy 122, such as was discussed above with reference to FIG. 5. Then, the surgeon may allow fixation structure 750 and expandable portion 540 to expand from their unexpanded state (i.e., a first dimension) to their expanded state (i.e., a second dimension). Any of the above, techniques discussed with reference to FIG. 2 may be used in permitting fixation structure 750 and expandable portion 540 to expand, such as, for example, using an expandable portion comprising inner and outer layers, an expandable portion that is a collar than can slide over carrier member 202, etc. . . .

In the specific embodiment shown in FIG. 7, fixation structure 750 in its expanded state circumferentially extends from carrier member 202 such that fixation structure 750 abuts the interior surface of outer portion 763 and the diameter of fixation structure 750 is greater than that of the outer portion 763 of facial portion 762. Fixation structure 750 has a diameter less than that of inner portion 764 and when inserted fits within inner portion 764. In this example, fixation structure 750 expands after insertion such that the fixation structure abuts and pushes on the inner surface of outer portion 763 to exert a longitudinal force that pushes stimulating lead assembly 118 toward cochleostomy 122 thus creating a compression and help prevent longitudinal movement of stimulating lead assembly 118 (that is, movement in a direction approximately parallel to longitudinal axis of stimulating lead assembly 118).

In other embodiments, fixation structure 705 may be manufactured from a material that does not expand in the presence of fluids. For example, in one such embodiment, fixation structure 750 comprises a flexible material having a diameter that is larger than the outer portion 763 of facial recess 762. In such embodiments, during implantation, flexible fixation structure 750 is forced through outer portion 763 and into inner portion 764. As fixation structure 750 attempts to exit cochlea 140, the compression of fixation structure 750 by the inner surface of bone 119 surrounding outer portion 763 creates the longitudinal anchor force that prevents movement of fixation structure 750 out of cochlea 140. In such embodiments, fixation structure 750 may comprise a flexible component such as silicone, polyurethane, PTFE, etc.

In yet other embodiments fixation structure 750 may comprise a flexible component or a malleable material such as a metal or a hard plastic or a shape-memory material that changes shape upon heating to body temperature or other catalyst such has IR or UV light, to anchor itself into the recess in bone 119, such as discussed above with reference to FIG. 6.

Although the embodiments of FIGS. 2, and 4-7 illustrate an expandable portion that is cylindrical in shape, in other embodiments the expandable portion may have alternative configurations. The below discussed FIGS. 8-12 provide exemplary alternative configurations for the expandable portion. Each of these alternative configurations may be used in any of the above-discussed embodiments of FIGS. 2 and 4-7.

Figure 8:
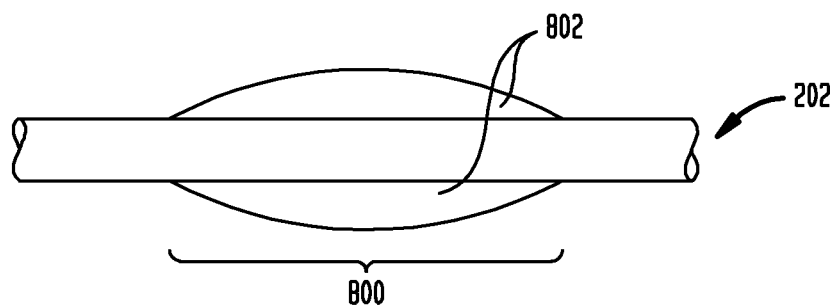
FIG. 8 is a side view of an exemplary configuration for the expandable portion that has a variable thickness, in accordance with embodiments of the present invention.

FIG. 8 is a side view of an exemplary configuration for the expandable portion that has a variable thickness, in accordance with an embodiment. As illustrated, expandable portion 800, in its expanded state, has a thickness that varies longitudinally along the length of carrier member 202. Expandable portion 800 may formed using techniques such as discussed above with reference to FIG. 2. In the illustrated example of FIG. 8, expandable portion 800 is formed by applying a layer of expandable material 802 to carrier member 202. This layer of expandable material 802 may surround carrier member 202 and have a thickness that is thicker in its longitudinal middle than at its edges. Although, illustrated, as a layer of expandable material applied to carrier member 202, in other embodiments, expandable portion 800 may be formed using other techniques, such as, for example, expandable portion 800 may be a separate member connecting an distal and proximal section of carrier member 202, a collar or ring, may comprise separate layers, etc.

Figure 9:
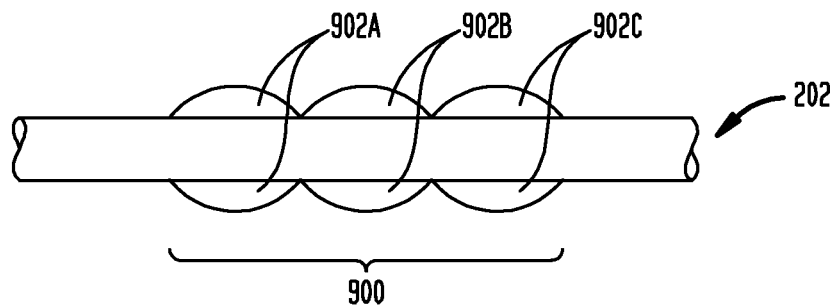
FIG. 9 is a side view of another exemplary configuration for the expandable portion that has a variable thickness, in accordance with embodiments of the present invention.

FIG. 9 is a side view of an exemplary configuration for the expandable portion that has a variable thickness, in accordance with an embodiment. Expandable portion 900 may be used, for example, as expandable portion 240 (FIG. 2).

As illustrated, expandable portion 900, in its expanded state, comprises three humps 902A, 902B, and 902C that extend radially from carrier member 202. In the illustrated example of FIG. 9, expandable portion 900 is formed by applying a layer of expandable material with a variable thickness to carrier member 202. Although illustrated as a layer of expandable material applied to carrier member 202, in other embodiments, expandable portion 900 may be formed using other techniques, such as, for example, those discussed above with reference to FIG. 2 (e.g., expandable portion 900 may be a separate member connecting an inner and outer section of carrier member 202, a collar or ring, may comprise separate layers, etc).

Use of an expandable portion with a variable thickness such as discussed above with reference to FIGS. 8-9 may be beneficial in helping avoid sharply swelling structures from migrating into the cochlea and potentially damaging the delicate structures inside the cochlea. They also may offer an improved seal and fixation in recipient's with an unevenly cut cochleostomy.

FIG. 10A illustrates a cross-sectional view of an exemplary configuration for expandable portion that may expand from only a portion(s) of the circumference of a carrier member, in accordance with an embodiment. Expandable portion 1000 may be used, for example, as expandable portion 240 (FIG. 2).

As illustrated in its expanded state, expandable portion 1000 comprises two opposing layers of expandable material 1002A and 1002B that extend radially from opposite sides the circumference of carrier member 202. Thus, prior to expansion, the cross-section of expandable portion 1000 may have a circular shaped, and then after expansion, the cross-section of expandable portion 1000 may have an oval shape. In an embodiment, expandable portion 1000 may be used with a cochleostomy 122 cut with a slot shape. FIG. 10B illustrates a cross-section of a slot shaped cochleostomy 1022, in accordance with an embodiment. During implantation of stimulating lead assembly 118, expandable portion 1000 may be positioned in cochleostomy 1022 so that when expanded, expandable portion 1000 will match the shape of cochleostomy 1022 (i.e., so that expandable portion 1000 expands along the long axis of the oval shaped cohcleostomy).

Use of an expandable portion and shaped cochleostomy, such as expandable portion 1000 and cochleostomy 1022, may help provide rotational orientation and stability of stimulating lead assembly 118. For example, as noted above, in an embodiment, electrode contacts 148 may be located on medial surface 216 of carrier member 202, which preferably should face the interior surface of cochlear 140 (FIG. 3A). Use of an expandable portion and shaped cochleostomy, such as expandable portion 1000 and cochleostomy 1022, may help maintain such a rotational orientation.

It should noted that expandable portion 1000 and shaped cochleostomy 1022 are but one example of an expandable portion with expandable material only a portion of the circumference of carrier member 202 and a matching shaped cochleostomy. For example, in other embodiments, the shaped cochleostomy may have other shapes, such as, an oval shape that is longer in the vertical axis, a rectangular shape, etc. Or, for example, expandable portion 1022 may have only single portion along its circumference with a layer of expandable material, multiple portions, etc.

In other embodiments, expandable portion 240 (FIG. 2) may be formed by applying a number of straight strips, spiral strips, spots, rings, or other patterns of expandable material along or around carrier member 202. Using such patterns may or may not form a full seal, but may help stabilize the location and orientation of stimulating lead assembly 118 in cochlea 140.

FIG. 11 illustrates a cross-section and side view of an exemplary configuration for the expandable portion that comprises strips of expandable material, in accordance with an embodiment. As illustrated, expandable portion 1100 comprises a plurality of strip of expandable material 1102A, 1102B, 1102C, and 1102D applied longitudinally along carrier member 202. Expandable portion 1100 may be used, for example, as expandable portion 240 (FIG. 2). Although illustrated as a layer of expandable material applied to carrier member 202, in other embodiments, expandable portion 1100 may be formed using other techniques, such as, for example, those discussed above with reference to FIG. 2 (e.g., expandable portion 1100 may be a separate member connecting an inner and outer section of carrier member 202, a collar or ring, may comprise separate layers, etc).

FIG. 12 illustrates a side view of an exemplary configuration for the expandable portion that comprises a plurality of rings, in accordance with an embodiment. Expandable portion 1200 may be used, for example, as expandable portion 240 (FIG. 2). As illustrated, expandable portion 1200 comprises three rings 1202A, 1202B, and 1202C that extend radially from and circumferentially around carrier member 202. Each of these rings 1202A-C may be formed by, for example, sliding a ring of expandable material over carrier member 202, by applying a layer of expandable material to carrier member 202, or by, for example, any of the other techniques discussed above (e.g., multiple layers of material, etc.). Further, the portions of expandable portion 1200 not covered by rings 1202A-C may or may not comprise expandable material. If entire expandable portion 1200 comprises expandable material, when exposed to fluid, the entire expandable portion may expand, as illustrated. Or, alternatively, only rings 1202A-C may comprise expandable material.

It is to be understood that the detailed description and specific examples, while indicating embodiments of the present invention, are given by way of illustration and not limitation. Many changes and modifications within the scope of the present invention may be made without departing from the spirit thereof, and the invention includes all such modifications.

What is claimed is:

1. A stimulating lead assembly for implantation into a recipient through an opening in a reference structure in the recipient, comprising:
   an carrier member, having a proximal and a distal end and at least one stimulation element disposed towards the distal end of said carrier member; and
   a self-expandable portion, disposed towards the proximal end of the carrier member, being expandable from a first dimension to a second dimension, and configured to interact with the reference structure at the opening in the reference structure, when said carrier member is implanted in the recipient and expanded to said second dimension, to physically secure the carrier member relative to the opening so as to substantially prevent movement of the carrier member.

2. The stimulating lead assembly of claim 1, wherein the expandable portion comprises a biocompatible material that expands from the first dimension to the second dimension in the presence of a fluid.

3. The stimulating lead assembly of claim 2, wherein the fluid is selected from the set of a body fluid and a saline solution.

4. The stimulating lead assembly of claim 3, wherein the biocompatible material comprises a hygroscopic material selected from the group consisting of a glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) (PEG/PAA) interpenetrating polymer network (IPN) hydrogel, polyethylene oxide-polybutylene terephthalate (PEO-PBT), a hyaluronic acid based hydrogel, high-molecular-weight polyacrylic acid (PAA), a PVA/chitosan blends, poly(hydroxy ethylmethacrylate), poly(ethylene glycol) (PEG) hydrogels, tetraethylene glycol diacrylate, polyethylene glycol methacrylate (PEGMA), cross-linkable (2-hydroxyethyl methacrylate) (HEMA), and poly(methyl acrylate-co-hydroxyethyl acrylate) hydrogel.

5. The stimulating lead assembly of claim 1, wherein the expandable portion comprises an inner layer and an outer layer, and wherein the inner layer comprises a hygroscopic material and the outer layer comprises a moisture resistant material.

6. The stimulating lead assembly of claim 5, wherein the outer layer comprises a membrane configured to delay or prevent the exposure of the inner layer to the fluid.

7. The stimulating lead assembly of claim 6, wherein the outer layer is configured to be dissolve in the presence of the fluid.

8. The stimulating lead assembly of claim 6, wherein the membrane comprises one or more seals that may be removed to permit fluid to reach the inner layer.

9. The stimulating lead assembly of claim 6, wherein the membrane is configured to be breached to permit fluid to reach the inner layer.

10. The stimulating lead assembly of claim 1, wherein the expandable portion comprises a layer of hygroscopic material applied to a portion of the carrier member.

11. The stimulating lead assembly of claim 1, wherein the expandable portion comprises a member comprising a hygroscopic material, and wherein the member connects a first portion of the carrier member and a second portion of the carrier member, and wherein the first and second portions of the carrier member comprises a material different than the hygroscopic material o the expandable portion.

12. The stimulating lead assembly of claim 1, wherein the expandable portion comprises a collar configured to fit over the carrier member.

13. The stimulating lead assembly of claim 1, wherein the expandable portion in configured to be implanted in the recipient adjacent to said reference structure and then expanded from the first to the second dimension to abut the reference structure such that when expanded to the second dimension the expandable portion prevents substantial translation of the carrier member.

14. The stimulating lead assembly of claim 1 wherein the expandable portion when implanted in the recipient and expanded to the second configuration is configured to seal the opening in the reference structure.

15. The stimulating lead assembly of claim 1, wherein the reference structure in the recipient comprises a biological structure.

16. The stimulating lead assembly of claim 15, wherein the reference structure is a cochlea.

17. The stimulating lead assembly of claim 16, wherein the cochlea comprises a bone comprising an inner surface and an outer surface, wherein the expandable portion is configured to interact with the inner surface, the stimulating lead assembly further comprising:
   a stop member configured to interact with the outer surface.

18. The stimulating lead assembly of claim 17, wherein the stimulating lead assembly is further configured for implantation into the recipient through an opening in a second reference structure in the recipient, and wherein the stimulating lead assembly further comprises:
   a fixation structure constructed and arranged to interact with the second reference structure when said carrier member is implanted in the recipient.

19. The stimulating lead assembly of claim 18, wherein the second reference structure is a temporal bone.

20. The stimulating lead assembly of claim 19, wherein the fixation structure comprises an expandable material that expands in the presence of a fluid.

21. The stimulating lead assembly of claim 20, wherein said fixation structure is further configured to interact with the second reference structure to prevent axial rotation of the carrier member.

22. The stimulating lead assembly of claim 1, wherein the expandable portion when expanded to the second dimension comprises a variable thickness along a longitudinal direction of the stimulating lead assembly.

23. The stimulating lead assembly of claim 22, wherein the thickness of the expandable portion is greater in a middle portion of the expandable portion than an edge portion of the expandable portion.

24. The stimulating lead assembly of claim 22, wherein the expandable portion comprises a plurality of rings of expandable material circumferentially surrounding the carrier member.

25. The stimulating lead assembly of claim 1, wherein the expandable portion comprises one or more strips of expandable material applied to a portion of the carrier member.

26. The stimulating lead assembly of claim 1, wherein the opening and a shape of the expandable portion in the second dimension are configured to interact when the stimulating lead assembly is implanted to prevent axial rotation of the carrier member.

27. The stimulating lead assembly of claim 1, wherein the expandable portion is positioned between the proximal end of the carrier member and the one or more stimulating elements disposed along said carrier member.

28. The stimulating lead assembly of claim 1, wherein the expandable portion comprises an indicia thereon.

29. The stimulating lead assembly of claim 1, wherein the stimulating element is an electrode contact.

30. A method of implanting a stimulating medical device, comprising:
preparing an appropriately configured opening in a reference structure of a recipient for implantation of an stimulating lead assembly comprising a carrier member, having a proximal end and a distal end, and a self-expandable portion disposed on a proximal portion of the carrier member;
inserting said carrier member through said opening in the recipient; and
expanding said expandable portion from a first dimension to a second dimension to interact with a portion of the reference structure at the opening in the reference structure to physically secure said carrier member relative to the opening of the recipient so as to substantially prevent movement of the carrier member.

31. The method of claim 30, wherein the expandable portion comprises a hygroscopic material.

32. The method of claim 30, wherein the reference structure is a cochlea.

* * * * *